United States Patent
Bukowska et al.

(10) Patent No.: US 6,214,336 B1
(45) Date of Patent: Apr. 10, 2001

(54) USE OF LACTOBACILLUS FOR REDUCTION OF THE FIBRINOGEN LEVEL IN BLOOD

(75) Inventors: Hanna Bukowska, Szczecin (PL); Marie-Louise Johansson, Lund (SE); Marek Naruszewicz, Zalesie Gorne (PL)

(73) Assignee: Probi AB, Lund (SE)

( * ) Notice: Subject to any disclaimer, the term of this patent is extended or adjusted under 35 U.S.C. 154(b) by 0 days.

(21) Appl. No.: 09/485,190

(22) PCT Filed: Jul. 30, 1998

(86) PCT No.: PCT/SE98/01423
§ 371 Date: Feb. 7, 2000
§ 102(e) Date: Feb. 7, 2000

(87) PCT Pub. No.: WO99/07827
PCT Pub. Date: Feb. 18, 1999

(30) Foreign Application Priority Data

Aug. 5, 1997 (SE) ................................... 9702860

(51) Int. Cl.[7] ............................. A01N 63/00; C12N 1/20; C12N 1/00
(52) U.S. Cl. .................................. 424/93.45; 435/252.9; 435/853; 435/856; 435/857
(58) Field of Search .................. 424/93.45; 435/252.9, 435/856, 857, 853

(56) References Cited

U.S. PATENT DOCUMENTS 5,474,932 * 12/1995 Bengmark et al. .
5,707,854 * 1/1998 Saito et al. .

FOREIGN PATENT DOCUMENTS 0 671 468    9/1995 (EP) .

06116155 * 4/1994 (JP) .

OTHER PUBLICATIONS

Bukowska et al. Atherosclerosis, 137(2): 437–8. Decrease in fibrinogen and LDL–cholesterol levels upon supplementation of diet with Lactobacillus plantarum in subjects with moderately elevated cholesterol, Apr. 1998.*

Bjornsson et al. Clinical Pharmacology and Therapeutics, 51(2), 193. Aspirin acetylates fibrinogen and has fibrinolytic effect in man, Mar. 1992.*

H. Bukowska, et al., Dialog Information Service, File 155, Dialog Accession No. 09595669, Medline Accession No. 98283630, 1 page, "Decrease in Fibrinogen and LDL–Cholesterol Levels Upon Supplementation of Diet with Lactobacillus Plantarum in Subjects with Moderately Elevated Cholesterol Letter", Apr. 1998.

H.J. Oakey, et al., Journal of Applied Bacteriology, vol. 78, No. 2, Dialog Information Service, File 5, Dialog Accession No. 115411251, Biosis Accession No. 98141251, 1 page, "Enzyme Production of Lactobacilli and the Potential Link with Infecti VE Endocarditis", 1995.

Derwent Abstracts, AN 96–421913, JP 8–208512, Aug. 13, 1996.

So–Young Park, et al., Chemical Abstracts, vol. 125, No. 15, Abstract No. 125:194329, "Effect of Various Lactic Acid Bacteria on the Serum Cholesterol Levels in Rats and Resistance to Acid, Bile and Antibiotics", Sept. 7, 1996.

* cited by examiner

Primary Examiner—Leon B. Lankford, Jr.
Assistant Examiner—Michele C. Flood
(74) Attorney, Agent, or Firm—Oblon, Spivak, McClelland, Maier & Neustadt, P.C.

(57) ABSTRACT

The invention refers to the use of a strain of Lactobacillus for the manufacture of a medicament for reduction of the fibrinogen level, and optionally cholesterol level, in blood. Said medicament can be utilized for the prophylaxis and/or treatment of circulatory diseases.

15 Claims, No Drawings

USE OF LACTOBACILLUS FOR REDUCTION OF THE FIBRINOGEN LEVEL IN BLOOD

The present invention refers to the use of strains of Lactobacillus being able to reduce the fibrinogen level, and optionally also the cholesterol level, in blood.

BACKGROUND OF THE INVENTION

Fibrinogen is a plasma protein, synthesized in the liver, which in the final step of the blood coagulation cascade by activated thrombin is converted into insoluble fibrin. Fibrin in turn, is in the fibrinolysis reaction decomposed by plasmin, also referred to as fibrinolysin, the normal mechanism for the removal of small fibrin clots from the circulation.

The plasma fibrinogen concentration increases gradually during normal aging from an average of 2.3 mg/ml at 20 years to 3.5 mg/ml at 70 years of age. The increase is coupled with about a 20% decrease in endogenous fibrinolytic activity over the same period. Under conditions of stress or trauma the blood fibrinogen level may double or triple within 48 hours. It has been confirmed that blood fibrinogen is a major determinant of blood and plasma viscosity in the microcirculation, of red cell and platelet aggregation and in the growth of atheromatous lesions. Blood fibrinogen levels are increased and the endogenous fibrinolytic activity decreased by conditions or factors which raise plasma free fatty acid, FFA, levels, see Pickart, L., in Pharmacology 23: 271–280, 1981.

An increased level of fibrinogen is associated with an increased erythrocyte sedimentation rate, which in turn since long has been correlated to a risk for ischemic heart diseases. In acute myocardial infarction the level of plasma fibrinogen as well as the level of free fatty acids are increased.

Fibrinogen as a cardiovascular risk factor is described by Ernst, E., et al., Annals of Internal Medicine 118: 956–963, 1993. In six prospective epidemiologic studies the correlation of fibrinogen levels on the subsequent incidence of myocardial infarction, stroke and peripheral arterial occlusive disease was assessed and the causality of the association was analysed. All prospective studies showed that fibrinogen was associated with subsequent myocardial infarction or stroke. It was concluded that fibrinogen is pathophysiologically related to cardiovascular events and can be considered a major cardiovascular risk factor.

There are several determinants of the fibrinogen level in health and disease, some of which can not be affected such as age, sex and heritage. Others which are amenable to change are lifestyle determinants such as smoking, sedentary life, diet and stress.

An increased cholesterol level, as well as an increased blood pressure are other important risk factors for heart diseases. Serum cholesterol levels generally refer to a combination of HDL, high density lipoproteins, and LDL, low density lipoproteins. Increased levels of LDL cholesterol may be associated with the pathogenesis of atherosclerosis while higher levels of HDL cholesterol appear to lower the risk of heart disease.

PRIOR ART

There are a wide variety of antilipidemic agents which in addition to a prolonged reduction in plasma FFA levels also reduce blood fibrinogen concentrations while enhancing fibrinolytic activity apparently by decreaseing hepatic synthesis of fibrinogen and antifibrinolysins, see Pickart, L., Pharmacology 23(5), 271–80, 1981. As examples of these agents, which are biochemically and structurally diverse, can be mentioned allylpropyl disulfide, the active principle from garlic and onion, acetylsalicylic acid and clofibrate, a fatty acid analogue. Most of these agents have annoying or serious side effects and more efficacious agents should be aimed at.

There are conflicting data regarding the potential hypocholesterolemic effect of fermented dairy products in man, and whether intake of these products has any significance in the prevention of coronary heart disease. Gilliland, S. E., et al., Applied and Environmental Microbiology, 49(2): 377–381, 1985, have found that some strains of Lactobacillus acidophilus, but not other, act directly on cholesterol in the gastrointestinal tract and may thus be beneficial in reducing serum cholesterol levels, and by this to lower the incidence of coronary heart disease. It is also reported that certain of said strains have the ability to deconjugate bile salts. In this study pigs were used as an animal model.

There is today no substance known that lowers the fibrinogen levels in patients at risk, safely and selectively.

DESCRIPTION OF THE INVENTION

It has now surprisingly been found that orally administered live Lactobacillus bacteria bring about a decrease in the serum fibrinogen level. The invention consequently refers to the use of a strain of Lactobacillus for the manufacture of a medicament for reduction of the fibrinogen level in blood in mammals including man.

Optionally the administered strain of Lactobacillus also brings about a decrease in the serum cholesterol level. is The invention therefore also refers to the use of a strain of Lactobacillus for the manufacture of a medicament for reduction of the fibrinogen level as well as the cholesterol level in blood.

The invention also refers to the use of a strain of Lactobacillus in combination with an antihyperlipoproteinemically active substance for the manufacture of a medicament for reduction of the fibrinogen level, as well as the cholesterol level, in blood. By this it will be possible to use a lower dose of the lipoprotein reducing drug, the administration of which is often associated with severe side effects.

In another aspect the invention refers to the use of a strain of Lactobacillus for the manufacture of a medicament for the prophylaxis and/or treatment of circulatory diseases, such as atherosclerosis, cardiovascular diseases, coronary heart disease, myocardial infarction, ischemic heart disease, stroke. A preferred strain of Lactobacillus should be able to survive the passage through the stomach to the gastrointestinal tract and be able to colonize in the intestines. Two factors seem to be crucial for the exertion of ecological effects of Lactobacilli. The first is the capacity to colonize the intestine, that is to survive in high numbers for a period of time after the last administration of live bacteria. The second is the capacity to bind directly to intestinal epithelial cells. This may be one of the factors that promotes colonization, but is not a prerequisite for colonization. The ability to adhere to the epithelium does not guarantee that the strain is able to colonize.

Examples of useful species of Lactobacillus are *L. plantarum* and *L. rhamnosus*. Different strains of of said lactobacilli are described in the International patent application WO 93/01823 refering to a process for isolation of strains of Lactobacillus having the ability to become established on the human intestinal mucosa in vivo and also to remain thereon after oral administration for at least 10 days. Said application especially refers to two new Lactobacillus strains, which have been deposited according to the Budapest Agreement at the DSM—Deutsche Sammlung von Mikroorganismen und Zellkulturen GmbH—, Braunschweig, Germany on Jul. 2, 1991, that is *L. plantarum* 299, number DSM 6595, and *L. casei* ssp. *rhamnosus* 271, number DSM 6594, as well as variants thereof. A preferred strain is Lactobacillus plantarum 299v, which has been deposited at the DSM on Mar. 16, 1995 under number DSM 9843. This strain as well as other strains of *L. plantarum* are described in the International patent application WO 96/29083.

The Lactobacillus strain can be administered in any food or pharmaceutical composition which can preserve the viability of the strain in the large intestine. The composition according to the invention can be administered in any suitable way, preferably orally or rectally, for example in the form of enema. It can also be administered enterally through a catheter inserted in the intestines via the stomach or directly in the intestines.

A carrier for the strain of Lactobacillus in the pharmaceutical composition is for example a physiologically acceptable substrate fermented by the bacterium in question, especially based on starch or milk. A suitable substrate could contain liquid or solid fibres which are not resorbed in the gastrointestinal tract. As an example of suitable, starch-containing substrates can be mentioned cereals, such as oats and wheat, corn, root vegetables such as potatoes and certain fruits such as green bananas. A preferred substrate for the pharmaceutical composition according to the invention, which also gives the composition an excellent nutritional value, is a nutrient solution based on oatmeal, for instance as described in WO 89/08405. The fermented product can also be mixed with a foodstuff, preferably based on fruit or berries, such as rose-hip, blueberries, strawberries, but also with inert solid or liquid substances, such as saline or water.

The treatment should take place once or several times daily for a continuous period. In order to give a detectable result the strain of Lactobacillus should be administered in a daily dose of not less than about $10^{10}$ bacteria.

Biological Test

The purpose of this study was to investigate the effect of a food product (ProViva®) containing *Lactobacillus plantarum* 299 v on serum lipid, especially LDL cholesterol, and fibrinogen levels in subjects with moderately elevated cholesterol concentrations.

Material and Methods

The ProViva® food product was a rose-hip drink containing oats (0.75 g of oat flour, that is 0.07 g of oat fibre/100 ml). The product contains approximately $5 \times 10^7$ cfu/ml of Lactobacillus plantarum 299 v and about 0.035 g of DL-lactic acid/100 ml. In the manufacturing of this product the fermented oats and the rose-hip drink were made separately and then mixed together in the ratio 5% (vol/vol) of fermented oats. (containing 18.5% (vol/vol) of oat flour) and 95% (vol/vol) of rose-hip drink. Plain rose-hip drink, consisting of rose-hip powder, sucrose, thickening agent, citric acid, ascorbic acid and water, was used as placebo. The two products were both manufactured by Skanemejerier (Lunnarp, Sweden).

The study was performed in 30 males aged 42.6±2.8 years, previously screened for gastointestinal symptoms, medication, tobacco smoking, dietary habits and alcohol consumption. Individuals with cardiovascular disease, diabetes mellitus and arterial hypertension were excluded from the study. Body mass, height, arterial blood pressure and pulse rate were recorded and blood was collected for biochemical tests. A double-blind study with placebo was designed and the participants were randomly divided into two equal groups, to be given ProViva® or placebo, respectively. Characteristics of the subjects of the study are given in Table 1 below.

Each subject consumed 200 ml ProViv® or placebo on each morning for six weeks and maintained the same lifestyle as before. At the end of said period the participants were examined and blood was again collected.

Cholesterol and triglyceride levels in serum were determined using enzyme kits (CHOD-PAP, GPO-PAP). HDL-cholesterol was measured after precipitation of lipoproteins containing apoB with phosphotungstic acid in the presence of $Mg^{2+}$. LDL-cholesterol was determined after precipitation of LDL with polyvinyl sulfate. Laboratory procedures were based on test kits from Boehringer-Mannheim. Glucose was measured using glucose oxidase and test kits from Analco (PAP) and plasma fibrinogen determinations followed the method of Clauss based on thrombin time (test kits from bioMerieux).

TABLE 1

Characteristics of the subjects in the two groups

| Parameter | ProViva ® | Placebo |
|---|---|---|
| Number | 15 | 15 |
| Age (years) | 43.0 ± 2.0 | 42.3 ± 3.0 |
| BMI (kg/m$^2$) | 26.6 ± 3.7 | 25.9 ± 2.6 |
| Systolic pressure (mm Hg) | 133 ± 12 | 125 ± 15 |
| Diastolic pressure (mm Hg) | 88 ± 7 | 83 ± 9 |

TABLE 2

Biochemical parameters in the subjects after consumption of ProViva ® or placebo

| Parameter | ProViva ® | | Placebo | |
|---|---|---|---|---|
| mg/dl | Before | After 6 weeks | Before | After 6 weeks |
| Triglycerides | 122 ± 61 | 121 ± 52 | 127 ± 42 | 112 ± 32 |
| Cholesterol | 233 ± 36 | 216 ± 33* | 216 ± 31 | 208 ± 0 |
| LDL-cholesterol | 156 ± 36 | 141 ± 34* | 140 ± 32 | 134 ± 41 |
| HDL-cholesterol | 47 ± 10 | 46 ± 10 | 48 ± 10 | 46 ± 8 |
| Glucose | 110 ± 11 | 112 ± 11 | 104 ± 10 | 109 ± 16 |
| Fibrinogen | 319 ± 82 | 276 ± 58** | 320 ± 85 | 307 ± 60 |

*p < 0.01
**p < 0.001

Results

There were no significant differences between the groups as to age, body mass index (BMI), systolic or diastolic blood pressure (Table 1). Results of the biochemical test are presented in Table 2. The initial concentrations of total cholesterol, LDL-cholesterol and fibrinogen were moderately elevated in both groups, but triglyceride and HDL-cholesterol values remained within normal limits. At this point no statistically significant differences between the groups were revealed.

The results are expressed in mg/dl. Mean values and standard deviations were calculated for the biochemical parameters and subjected to the unpaired Student's t-test between groups or the paired test within each group. The level of significance was taken as $p < 0.05$. After six weeks of the experiment the level of fibrinogen in the ProViva® group fell from 319±82 to 276±58 mg/dl (p<0.001), representing a reduction of 13.5% vs. the initial value. Similarly, the levels of total cholesterol and LDL-cholesterol were reduced by 7.3% (233±33 to 216±31) and 9.6% (156±36 to 141±34), respectively. Triglyceride, glucose and HDL-cholesterol levels remained unchanged in this group.

In the placebo group no statistically significant differences between the initial and final values were observed.

The present study confirms earlier observations that food products containing certain strains of Lactobacillus reduce blood cholesterol levels. However, for the first time it was found that a strain of Lactobacillus is effective in reducing the fibrinogen level. In conclusion, diet supplemenation with Lactobacillus could be beneficial to patients with moderately elevated cholesterol concentrations, reducing the risk of cardiovascular disease.

It has already been confirmed that fibrinogen is an independent risk factor of ischemic heart disease and its level in blood is regulated by genetic and environmental factors. The finding that ProViva decreases both the level of fibrinogen and cholesterol may make it a promising food product in the early prevention of ischemic heart disease.

What is claimed is:

1. A method of reducing the level of fibrinogen in the blood of a mammal, comprising administering to a mammal in need of reduced fibrinogen levels an effective amount of a strain of Lactobacillus.

2. The method of claim 1 wherein the mammal is a human.

3. The method of claim 1 wherein the Lactobacillus is *Lactobacillus plantarum* or *Lactobacillus rhamnosus*.

4. The method of claim 3 wherein the strain of Lactobacillus is *Lactobacillus plantarum* 299v, deposited under the accession number DSM 9843.

5. A method of reducing the levels of both fibrinogen and cholesterol in the blood of a mammal, comprising administering to a mammal in need thereof an effective amount of a strain of Lactobacillus.

6. The method of claim 5 wherein the mammal is a human.

7. The method of claim 5 wherein the Lactobacillus is *Lactobacillus plantarum* or *Lactobacillus rhamnosus*.

8. The method of claim 7 wherein the strain of Lactobacillus is *Lactobacillus plantarum* 299v, deposited under the accession number DSM 9843.

9. The method of claim 5 wherein the Lactobacillus is administered in combination with an antihyperlipoproteinemically active substance.

10. A method of preventing and/or treating circulatory disease in a mammal caused by increased fibrinogen levels, comprising administering to a mammal in need thereof an effective amount of a strain of Lactobacillus.

11. The method of claim 10 wherein the circulatory disease is selected from the group consisting of atherosclerosis, cardiovascular disease, coronary heart disease, myocardial infarction, ischemic heart disease, and stroke.

12. The method of claim 10 wherein the mammal is a human.

13. The method of claim 10 wherein the Lactobacillus is *Lactobacillus plantarum* or *Lactobacillus rhamnosus*.

14. The method of claim 13 wherein the strain of Lactobacillus is *Lactobacillus plantarum* 299v, deposited under the accession number DSM 9843.

15. The method of claim 10 wherein the Lactobacillus is administered in combination with an antihyperlipoproteinemically active substance.

* * * * *